US00PP28847P3

(12) United States Plant Patent
Spruit

(10) Patent No.: US PP28,847 P3
(45) Date of Patent: Jan. 2, 2018

(54) ***ZAMIOCULCAS* PLANT NAMED 'DARK ZAMICRO'**

(50) Latin Name: *Zamioculcas zamiifolia*
Varietal Denomination: Dark Zamicro

(71) Applicant: Adrianus Theodorus Spruit, Aarlanderveen (NL)

(72) Inventor: Adrianus Theodorus Spruit, Aarlanderveen (NL)

(73) Assignee: Aardam B.V., Aarlanderveen (NL)

( * ) Notice: Subject to any disclaimer, the term of this patent is extended or adjusted under 35 U.S.C. 154(b) by 36 days.

(21) Appl. No.: 14/999,322

(22) Filed: Apr. 25, 2016

(65) Prior Publication Data

US 2017/0311530 P1 Oct. 26, 2017

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct *Zamioculcas* plant named 'Dark Zamicro', characterized by its broadly upright and compact growth habit; relatively small leaflets; and glossy leaflets that are close to pure black in color.

2 Drawing Sheets

Botanical designation: *Zamioculcas zamiifolia.*
Cultivar denomination: 'DARK ZAMICRO'.

BACKGROUND OF THE INVENTION

The present invention relates to a new and distinct *Zamioculcas* plant, botanically known as *Zamioculcas zamiifolia*, and hereinafter referred to by the name 'Dark Zamicro'.

The new *Zamioculcas* plant is a naturally-occurring whole plant mutation of *Zamioculcas zamiifolia* 'Zamicro', disclosed in U.S. Plant Pat. No. 19,314. The new *Zamioculcas* plant was discovered and selected by the Inventor as a single plant from within a population of plants of 'Zamicro' in a controlled environment in Aarlanderveen, The Netherlands in September, 2013.

Asexual reproduction of the new *Zamioculcas* plant by vegetative cuttings in a controlled environment in Aarlanderveen, The Netherlands since November, 2013, has shown that the unique features of this new *Zamioculcas* plant are stable and reproduced true to type in successive generations.

SUMMARY OF THE INVENTION

The cultivar Dark Zamicro has not been observed under all possible combinations of environmental conditions and cultural practices. The phenotype may vary somewhat with variations in environment and cultural practices such as temperature and light intensity without, however, any variance in genotype.

The following traits have been repeatedly observed and are determined to be the unique characteristics of 'Dark Zamicro'. These characteristics in combination distinguish 'Dark Zamicro' as a new and distinct *Zamioculcas* plant:

1. Broadly upright and compact growth habit.
2. Relatively small leaflets.
3. Glossy leaflets that are close to pure black in color.

Plants of the new *Zamioculcas* can be compared to plants of the parent, 'Zamicro'. Plants of the new *Zamioculcas* differ primarily from plants of 'Zamicro' in leaf color as plants of 'Zamicro' have dark green-colored leaves.

Plants of the new *Zamioculcas* can be compared to plants of *Zamioculcas zamiifolia* 'Black Zamio', not patented. In side-by-side comparisons conducted in Aarlanderveen, The Netherlands, plants of the new *Zamioculcas* differed from plants of 'Black Zamio' in the following characteristics:

1. Plants of the new *Zamioculcas* were more compact and shorter than plants of 'Black Zamio'.
2. Plants of the new *Zamioculcas* had smaller leaves than plants of 'Black Zamio'.

BRIEF DESCRIPTION OF THE PHOTOGRAPHS

The accompanying colored photographs illustrate the overall appearance of the new *Zamioculcas* showing the colors as true as it is reasonably possible to obtain in colored reproductions of this type. Colors in the photographs may differ slightly from the color values cited in the detailed botanical description which accurately describe the colors of the new *Zamioculcas.*

The photograph on the first sheet comprises a side perspective view of a typical plant of 'Dark Zamicro' grown in a container.

The photograph on the second sheet is a close-up view of a typical leaf and the upper and lower surfaces of typical leaflets of 'Dark Zamicro'.

DETAILED BOTANICAL DESCRIPTION

The aforementioned photographs and following observations, measurements and values describe plants of the new *Zamioculcas* grown during the winter 12.6 cm by 11.3 cm square containers in a glass-covered greenhouse in Aarlanderveen, The Netherlands and under cultural practices which closely approximate commercial production. During the production of the plants, day temperatures ranged from 20° C. to 30° C. and night temperatures ranged from 18° C. to 21° C. Plants were eight months old when the photographs and the description were taken. In the detailed description, color references are made to The Royal Horticultural Society Colour Chart, 2015 Edition, except where general terms of ordinary dictionary significance are used.

Botanical classification: *Zamioculcas zamiifolia* 'Dark Zamicro'.

Parentage: Naturally-occurring whole plant mutation of *Zamioculcas zamiifolia* 'Zamicro', disclosed in U.S. Plant Pat. No. 19,314.

Propagation:

*Type*.—By vegetative cuttings.

*Time to initiate roots, summer*.—About 21 days at temperatures about 20° C. to 30° C.

*Time to initiate roots, winter*.—About 31 days at temperatures about 20° C. to 25° C.

*Time to produce a rooted young plant, summer*.—About 140 days at temperatures about 22° C. to 30° C.

*Time to produce a rooted young plant, winter*.—About 200 days at temperatures about 20° C. to 25° C.

*Root description*.—Medium in thickness to thick, fleshy; typically white to light brown in color, actual color of the roots is dependent on substrate composition, water quality, fertilizer type and formulation, substrate temperature and physiological age of roots.

*Rooting habit*.—Medium density; not freely branching.

Plant description:

*Plant and growth habit*.—Broadly upright and compact growth habit; inverted triangle to roughly obovate; stemless; pinnately compound leaves developing in loose basal rosettes; typically about four basal rosettes develop per plant; suitable for 9-cm and larger containers; low vigor to moderately vigorous.

*Plant height*.—About 39.3 cm.

*Plant diameter*.—About 29.8 cm.

Leaf description:

*Arrangement*.—Pinnately compound; about 13 leaflets per leaf; leaflets sessile.

*Leaf length*.—About 37.8 cm.

*Leaf width*.—About 9.3 cm.

*Leaflet length*.—About 7.1 cm.

*Leaflet width*.—About 2.5 cm.

*Leaf shape*.—Oblong.

*Leaflet shape*.—Elliptic to ovate; slightly to moderately concave.

*Leaflet apex*.—Acute to short apiculate.

*Leaflet base*.—Attenuate.

*Leaflet margin*.—Entire.

*Leaflet texture, upper and lower surfaces*.—Glabrous, smooth; thick.

*Leaflet texture, upper surface*.—Very glossy.

*Leaflet texture, lower surface*.—Moderately glossy.

*Leaflet venation pattern*.—Pinnate.

*Color*.—Developing leaflets, upper surface: Close to between 143B and 144A to 144C. Developing leaflets, lower surface: Close to 144A. Fully expanded leaflets, upper surface: Close to between N189A and 203A, closest to 203A; venation, close to between N189A and 203A, closest to 203A. Fully expanded leaflets, lower surface: Close to between 147A and N189A, closest to darker than 147A; venation, 148A to darker than 148A.

*Rachis length, base of leaf to lowest leaflet*.—About 16.7 cm.

*Rachis diameter, at base of leaf*.—About 1.4 cm.

*Rachis diameter, halfway between base of leaf and lowest leaflet*.—About 9 mm.

*Rachis diameter, at lowest leaflet*.—About 6.5 mm.

*Rachis strength*.—Moderately strong.

*Rachis texture*.—Smooth, glabrous.

*Rachis luster*.—Slightly glossy.

*Rachis color*.—Close to 148A to 148B.

Flower description: Flower initiation and development has not been observed on plants of the new *Zamioculcas*.

Temperature tolerance: Plants of the new *Zamioculcas* have been observed to tolerate high temperatures about 40° C. and to suitable for USDA Hardiness Zones 10 to 12.

Pathogen & pest resistance: Plants of the new *Zamioculcas* have not been observed to be resistant to pathogens and pests common to *Zamioculcas* plants.

It is claimed:

1. A new and distinct *Zamioculcas* plant named 'Dark Zamicro' as illustrated and described.

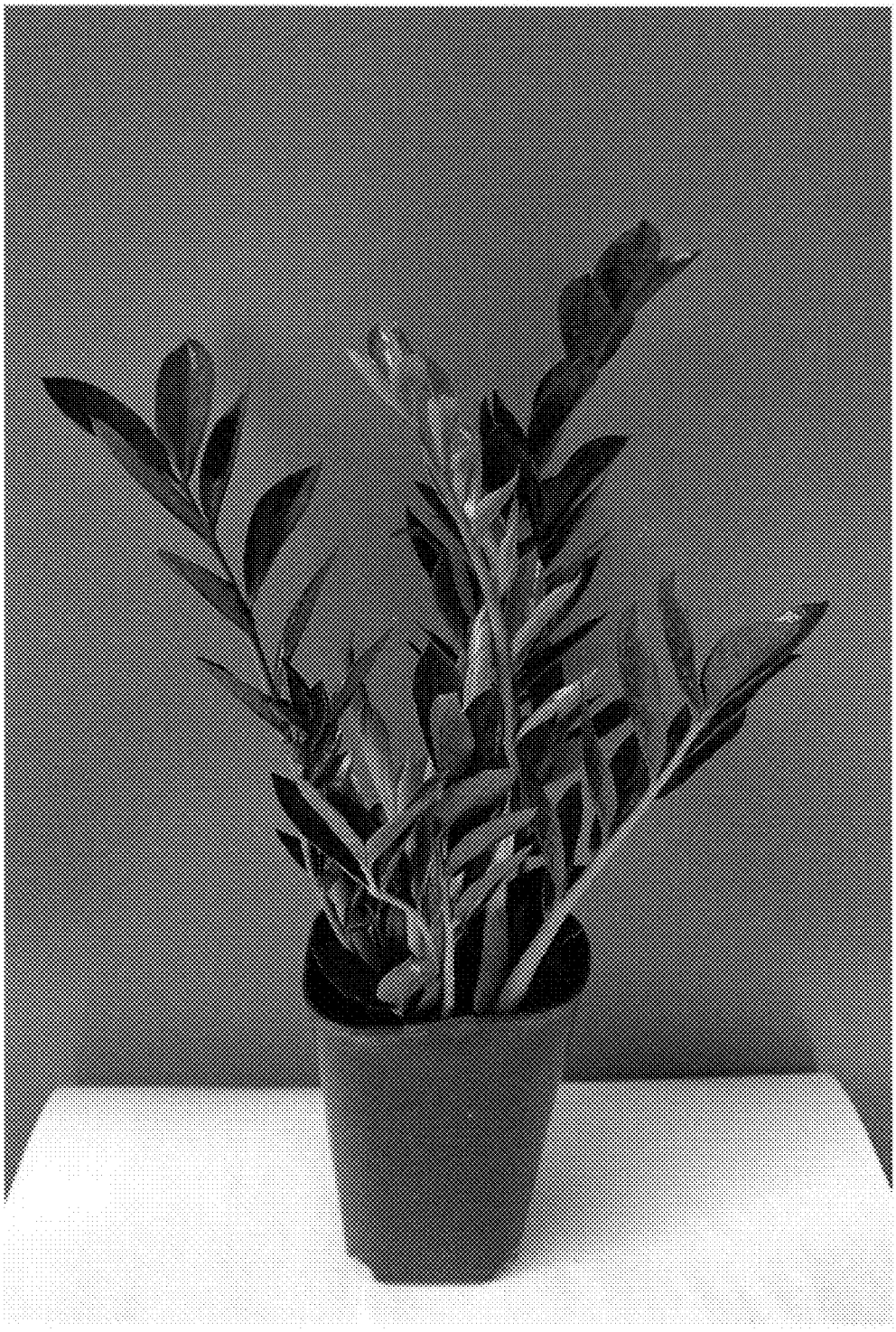

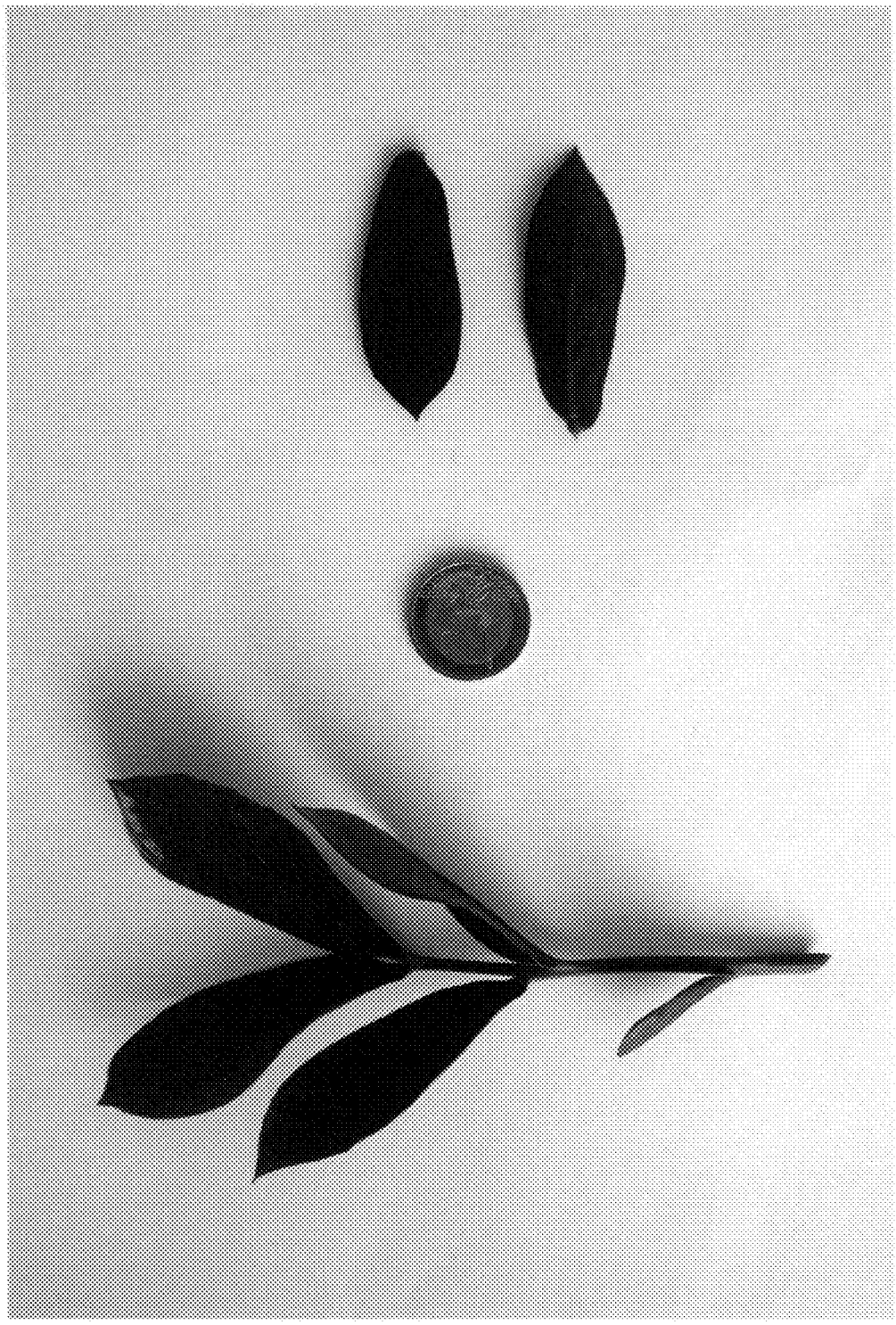

* * * * *